United States Patent [19]

Salpekar et al.

[11] Patent Number: 4,757,090
[45] Date of Patent: Jul. 12, 1988

[54] DIRECT TABLETING ACETAMINOPHEN COMPOSITIONS

[75] Inventors: Anil M. Salpekar, Creve Coeur; Larry E. Denton, Fenton, both of Mo.

[73] Assignee: Mallinckrodt, Inc., St. Louis, Mo.

[21] Appl. No.: 14,306

[22] Filed: Feb. 13, 1987

Related U.S. Application Data

[63] Continuation of Ser. No. 884,911, Jul. 14, 1986, Pat. No. 4,661,521, which is a continuation of Ser. No. 605,160, Apr. 30, 1984, abandoned.

[51] Int. Cl.$^4$ .................................................. A61K 9/14
[52] U.S. Cl. .................................... 514/613; 264/118; 424/80; 424/465; 514/849
[58] Field of Search ................ 514/613, 849; 264/118; 424/80, 465

[56] References Cited

U.S. PATENT DOCUMENTS

| | | | |
|---|---|---|---|
| 2,798,838 | 7/1957 | Robinson | 167/82 |
| 2,876,160 | 3/1959 | Schoch et al. | 167/82 |
| 3,181,998 | 5/1965 | Kanig | 167/82 |
| 3,453,368 | 7/1969 | Magid | 514/474 |
| 3,499,962 | 3/1970 | Wurzburg et al. | 424/489 |
| 3,786,123 | 1/1974 | Katzen | 264/53 |
| 3,851,032 | 11/1974 | Andrews et al. | 264/109 |
| 3,923,974 | 12/1975 | Andrews et al. | 424/80 |
| 4,072,535 | 2/1978 | Short et al. | 106/210 |
| 4,327,080 | 4/1982 | Wong et al. | 424/80 |
| 4,661,521 | 4/1987 | Salpekar et al. | 424/465 |

FOREIGN PATENT DOCUMENTS

| | | |
|---|---|---|
| 0040472 | 11/1981 | European Pat. Off. . |
| 1287431 | 8/1972 | United Kingdom . |
| 1390032 | 4/1975 | United Kingdom . |
| 2090739 | 7/1982 | United Kingdom . |

OTHER PUBLICATIONS

Salpekar, Anil M.: "A Study of Some Important Aspects of Tablet Lubrication"-Ph.D. Dissertion/Univ. Maryland, 1975.
Starch 1500 ® Colorcon, Inc. brochure, 14 pages (including front and back covers).
Dr. rer. nat. Paul Heinz List, "Arzneiformenlehr", 1976, p. 74, (Original and translation) [2 pages].
Lactose-U.S.P. Fast-FLo, Foremost Foods Company brochure, 1977, 8 pages.
"Plasdone ® Povidone USP", GAF Corp. Bulletin No. 2302-2310, (1981), 14 pages.
"Prototype Formulation: Acetaminophen Tablets", Colorcon, Inc. Technical Data Bulletin, (2/81), 2 pages.
"Evaluation of Starch 1500 As a Gradulation Binder in the Formulation of Acetaminophen Tablets", Colorcon, Inc. Technical Data Bulletin, (2/81-per private communication dated Feb. 15, 1984, Anil M. Salpekar, 6 pages.

*Primary Examiner*—Ronald W. Griffin
*Attorney, Agent, or Firm*—Bernard, Rothwell & Brown

[57] ABSTRACT

An N-acetyl-p-aminophenol composition capable of being directly formed into a tablet having high hardness, short disintegration time and short dissolution time is disclosed. The composition includes N-acetyl-p-aminophenol, a pharmaceutically acceptable pregelatinized starch, a pharmaceutically acceptable lubricant, water and optionally an auxiliary binder such as polyvinylpyrrolidone. Also disclosed is a method for preparing the composition which includes drying a fluidized bed of the composition in a fluid bed granulator-dryer.

7 Claims, No Drawings

4,757,090

DIRECT TABLETING ACETAMINOPHEN COMPOSITIONS

This is a continuation of application Ser. No. 884,911, filed July 14, 1986, now U.S. Pat. No. 4,661,521, which is a continuation of application Ser. No. 605,160, filed Apr. 30, 1984, now abandoned.

TECHNICAL FIELD

The invention herein lies in the art of pharmaceuticals, and is more particularly directed to a process and composition useful in direct tableting. Specifically, a process is disclosed for granulating and drying a pharmaceutical preparation with a fluidized bed apparatus. The compositions of the invention contain one or more binders and a lubricant for facilitating the tableting process.

BACKGROUND ART

The present invention relates to an N-acetyl-p-aminophenol composition containing pregelatinized starch, to a method for preparing the composition and to orally administerable analgesic tablets formed from the composition. N-acetyl-p-aminophenol (hereinafter often referred to as either acetaminophen or simply APAP) is generally non-compressible, especially in forming orally administerable tablets. Accordingly, there is a substantial need in the art for a direct tableting, free-flowing particulate APAP composition capable of being directly formed into a tablet having high hardness, short disintegration time and short dissolution time. It has now been found by practice of the present invention that such APAP compositions can be formed.

Advantageously, the composition of the present invention can be directly formed into tablets by tablet operators without the need for admixing tableting adjuvants or aids. In various embodiments of the present composition described hereinbelow, the mutually conflicting needs for tablets having high hardness and short disintegration and/or dissolution times can be met.

DESCRIPTION OF THE INVENTION

Generally stated, the present invention provides a direct tableting, free-flowing particulate pharmaceutical composition capable of being directly formed into a tablet having high hardness, short disintegration time, and short dissolution time, the composition comprising as components thereof:
(a) N-acetyl-p-aminophenol,
(b) A pharmaceutically acceptable pregelatinized starch in an amount effective for imparting said hardness, disintegration time, and dissolution time,
(c) A pharmaceutically acceptable lubricant in an amount at least sufficient to impart effective mold release properties to said tablet, and
(d) Water in an amount from about 1.0 to about 2.5 percent based on the total weight of the composition,
said components being distributed throughout the particles of said composition in at least approximately the same distribution achieved when the composition is prepared by a fluid bed granulation technique using said components (a), (b) and (c).

In another aspect, generally stated, this invention provides for a method for preparing a direct tableting, free-flowing particulate N-acetyl-p-aminophenol composition capable of being directly formed into a tablet having high hardness, short disintegration time and short dissolution time, said method comprising:
(a) charging the N-acetyl-p-aminophenol and a portion of the pregelatinized starch to a fluid bed granulator-dryer,
(b) fluidizing the N-acetyl-p-aminophenol and pregelatinized starch until thoroughly blended,
(c) dispersing the remaining pregelatinized starch and water with a high shear mixer to form a slurry having from about 5 to about 15 percent by weight solids,
(d) spraying the starch dispersion onto the fluidized bed of N-acetyl-p-aminophenol and pregelatinized starch at a rate sufficient to maintain the powder bed moisture between about 5 and about 20 percent by weight,
(e) continuing drying after all the dispersion is sprayed to reach a bed moisture of about 5 percent by weight,
(f) stopping fluidization to add the lubricant,
(g) resuming fluidization until the moisture level of the bed is between about 1.0 and about 2.5 percent by weight,
(h) sizing the material to the desired particle size distribution.

Alternatively, the lubricant may be blended with the material after the sizing step in a suitable device such as a double cone blender.

DETAILED DESCRIPTION OF THE INVENTION AND OF THE MANNER AND PROCESS OF MAKING AND USING IT

The N-acetyl-p-aminophenol component of the present invention is preferably provided in finely divided form, i.e., the APAP is preferably of small particle size. For example, it has been found that if more than 30 percent by weight of the APAP particles are larger than 60 mesh (U.S. Standard Sieve) then the compressibility of the granulation is adversely affected. For use in the present invention, preferably all of the APAP particles will pass through a 60 mesh screen, more preferably 75 percent will pass through an 80 mesh screen.

The pregelatinized starch component of the direct tableting composition can be obtained from any well known starch manufacturer such as, for example, the National Starch Corporation. Pregelatinized starches useful in the invention must meet all the NF·XV requirements for such starches.

The pregelatinized starch serves to impart good binder and disintegrant properties as well as a good balance thereof to the composition, which can be directly tableted to form tablets having high hardness, short disintegration time and short dissolution time.

The term "direct tableting" and terms of like import, as used herein, mean that the composition can be formed into a tablet using well known tableting apparatus and processes without need for addition of any adjuvant material to the composition. As used herein, the term "kp" means kiloponds, a well known unit of force for expressing hardness or crushing strength of pharmaceutical tablets when such hardness is determined on a Schleuniger Tablet Hardness Tester.

The pregelatinized starch is included in an amount effective for imparting to the composition the capability of being formed into tablets having high hardness (e.g., about 8 kp or more), short disintegration time (e.g., about 10 minutes or less) and short dissolution time (e.g., about 20 minutes or less for 80 percent or more of the APAP to dissolve). In general, such effective amount of pregelatinized starch is from about 5 or less to about 15 or more parts per 100 parts of the composition, more preferably, from about 6 to about 10 parts per 100 parts of the composition.

The lubricant component may be any pharmaceutically acceptable lubricant, which may be, e.g., hydrophilic or hydrophobic. This component is present in a lubricating amount at least sufficient to impart mold release properties to tablets formed in the compositions and preferably insufficient to increase disintegration time and dissolution time of such tablets, and preferably insufficient to decrease the hardness obtainable for tablets formed from compositions of this invention containing lower lubricating amounts of the same lubricant.

Suitable lubricants for use as the lubricating component include, for example, stearic acid, metallic stearate (such as sodium, calcium, magnesium and zinc stearate, etc.), sodium lauryl sulfate, polyethylene glycol, hydrogenated vegetable oils, talc and compatible mixtures of two or more such materials. Stearic acid is preferred.

In general, the stearic acid or other lubricant component may be present in an amount from about 0.10 to about 1 percent, more preferably from about 0.25 to about 0.75 percent, and most preferably about 0.5 percent, based on the total dry weight of the composition.

The composition also includes water in an amount effective for aid in direct tableting. Such effective amount is, in general, found to be from about 1.0 to about 2.5 percent based on the total weight of the composition, preferably from about 1.3 to about 2.2 percent on the same basis.

Optionally, the composition may further include a pharmaceutically acceptable compressibility-promoting binder as an additional binding agent in an amount effective for increasing the obtainable hardness of tablets formed from the composition. Materials suitable for use as the optionally included, but preferably included additional binder agent include, for example, starch paste (fully gelatinized starch), polyvinylpyrrolidone, hydroxypropylmethylcellulose, hydroxypropylcellulose, gelatin, natural gums (e.g., gum acacia, gum tragacanth, etc.), sucrose, mannitol, ethylcellulose, synthetic polymer binders commonly used in the industry, and compatible mixtures of two or more such materials. Polyvinylpyrrolidone (PVP) is preferred (preferably PVP ® K-29-32.).

In general, such effective amount of optional binder is from about 0.5 or less to about 2.5 or more parts, preferably not more than 1.5, more preferably about 1.0 parts per 100 parts of the composition.

A preferred embodiment includes the following components in the amounts indicated:

| Components | Approximate Amounts |
| --- | --- |
| APAP (acetaminophen), USP | 84.0–94.9 |
| Pregelatinized starch, NF | 15.0–5.0 |
| Stearic acid, NF | 1.0–0.1 |

The amounts shown are in parts per 100 parts (dry basis) of the composition.

The best embodiment composition of this invention contemplated at the time of executing this patent application is as follows, wherein the amounts given are in parts per 100 parts by weight (dry basis) of the composition:

| Components | Approximate Amounts |
| --- | --- |
| APAP (acetaminophen), USP | 90 |

-continued

| Components | Approximate Amounts |
| --- | --- |
| Pregelatinized starch, NF | 9.5 |
| Stearic acid, NF | 0.5 |

Such composition of the last-given embodiment can be repeatedly, in general, formed into tablets having hardness of 8 kp or more and having a disintegration time of 5 minutes or less at about 8–10 kp hardness.

In use, the compositions of this invention advantageously may be composited with other active and/or inert ingredients, either prior to compositing the components to form the composition or after the composition is formed (e.g., by dry blending the composition with such ingredients). Thereafter the compositions may be directly compressed into tablets having eminently suitable values of hardness and disintegration time for a variety of end-use applications.

The compositions of this invention are preferably made by the method mentioned above, which includes the use of a fluid bed granulator-dryer. A suitable sized fluid bed granulator-dryer (FBGD) is charged with the acetaminophen and a portion of the pregelatinized starch. The amount of the pregelatinized starch added is from about 2 to about 6 percent by weight based on the total weight of the composition. Preferably, about 3.5 percent on the above basis is charged to the fluid bed. The materials are fluidized until thoroughly blended. The remaining pregelatinized starch, i.e., about 6 percent, which was not added to the fluid bed is dispersed in water to yield a slurry of between about 5 and about 10 weight percent solids, using a high shear mixer. Other components, if present, may be added either to the dry blend or the slurry, as needed. The starch dispersion is then sprayed onto the fluidized bed of acetaminophen/pregelatinized starch at a rate sufficient to maintain the powder bed moisture between about 5 and about 20 weight percent, and preferably between about 10 and about 16 weight percent. After complete addition of the dispersion to the fluid bed, the fluidization is continued until the bed moisture is about 3 to about 5 percent. The fluidization is then halted, the stearic acid or other lubricant is added, and the fluidization resumed until the moisture level of the bed is reduced to between about 1.0 and about 2.5 weight percent, and preferably from about 1.3 to about 2.2 weight percent. The fluidization is then terminated and the material is sized using suitable equipment, such as a Glatt Quick Sieve or Stoke's Granulator, to the desired particle size distribution. Alternatively, the lubricant may be blended with the material after granulation and sizing using a suitable blender, such as a double-cone blender.

The fluid bed granulator-dryer is operated under the following conditions: a stream of heated air is introduced from the bottom of the fluid bed at a sufficient velocity to fluidize the powder bed and at a temperature sufficient to heat the powder bed to between about 20° C. to about 50° C. The air velocity, inlet air temperature and the powder bed temperature are dependent on the batch size, dew point of air, and spray rate of the binder solution during the granulation phase and therefore are adjusted accordingly. The particle size of the bed material is influenced by the atomization pressure used to spray the granulating liquid as well as by the moisture level of the fluid bed during the granulation phase. By adjusting operative parameters, the desired particle size distribution for the granulation can be obtained. A further sizing of the dry granulation (to obtain a narrow particle size distribution) may be achieved using a Glatt Quick Sieve or other suitable sizing equipment.

The following examples and tables illustrate the invention. As used herein, the following terms have the meanings indicated:

(a) "Disintegration time" means the time measured using the disintegration-time test method set forth in U.S. Pharmacoepia (hereinafter "USP") XX for uncoated tablets except that the disks are not employed;

(b) "Dissolution-time" means the time measured using the dissolution-time test method set forth in USP XX for APAP tablets;

(c) "Hardness" means the hardness measured on a Schleuniger Hardness Tester;

(d) "Maximum hardness" means the maximum hardness at which the tablets are substantially free of lamination;

(e) "Friability" means the friability measured on a Roche Friabulator for 20 tablets and 100 revolutions.

Unless otherwise indicated, all tablet hardness values are averages for ten tablets and all tablet weights are averages obtained by weighing 20 tablets as a whole and dividing by 20. Further, unless otherwise indicated, tablet disintegration times were measured for tablets having about 9 kp hardness.

Example I

Using the procedure described above, a directly-tabletable granular composition was prepared in a fluid bed granulator-dryer (Glatt Air Techniques, Inc., Model WSG-300) from the following components:

| Components | Approximate Amounts |
|---|---|
| APAP (acetaminophen), USP | 90.0% |
| Pregelanitized starch, NF | 8.5% |
| Stearic acid, NF | 0.5% |
| Polyvinylpyrrolidone, USP | 1.0% |

The batch size (exclusive of added water) was 333 kg. The composition was dried to a final moisture content of 2.3% and had a bulk density of 0.52 g/cc. The granular composition was sized to the following particle size distribution on a Glatt Quick Sieve:

| Particle Size Distribution: | |
|---|---|
| Mesh | Cum. % Retained |
| +20 | 15.5 |
| +40 | 80.1 |
| +60 | 92.2 |
| +80 | 95.2 |
| −80 | 4.8 |
| | 100.0% |

Assay = 91.1%

The granular composition was directly formed into tablets of two sizes, which had the tablet properties given in Table I.

Example II

Using the procedure described above, a directly tabletable granular composition was prepared in a lab-scale fluid bed granulator-dryer (Aeromatic, Inc., Model STREA-1) from the components indicated below. The batch size (exclusive of added water) was 0.78 kg.

| Components | Approximate Amounts |
|---|---|
| Acetaminophen | 90.0% |
| Sorbitol (as 70% solution) | 3.0% |
| Pregelatinized Starch | 6.5% |
| Stearic Acid | 0.5% |

Following addition of the stearic acid, the composition was dried to a final moisture content of 1.3%, with a bulk density of 0.41 g/cc, and sized. The composition produced in this manner can be directly formed into tablets.

Example III

Using the procedure described above, a directly tabletable granular composition was prepared in a lab-scale fluid bed granulator-dryer (Aeromatic, Inc., Model STREA-1) from the components indicated below. The batch size (exclusive of added water) was 0.78 kg.

| Components | Approximate Amounts |
|---|---|
| Acetaminophen | 90.0% |
| Methocel (Hydroxypropylmethylcellulose) | 1.0% |
| Pregelatinized Starch | 8.5% |
| Stearic Acid | 0.5% |

Following addition of the stearic acid, the composition was dried to a final moisture content of 2.3%, and sized. The composition produced in this manner can be directly formed into tablets.

Example IV

Using the preferred procedure described above, a directly tabletable granular composition was prepared in a fluid bed granulator-dryer (Glatt Air Techniques, Inc., Model WSG-300) from the components listed below. The dry ingredients were charged to the product bowl and fluidized. The granulating liquid was prepared in a steam jacketed tank using a high shear mixer and sprayed onto the fluidized bed. After the bed moisture reached about 2–5%, fluidization was stopped and the stearic acid was added. Fluidization was resumed and drying continued until the granules reached the final moisture content indicated below. Tablets produced from the graulated composition had the properties given in Table II.

| | Weight/Batch |
|---|---|
| Granulating Liquid Ingredient | |
| Povidone, USP (K-29-32) | 4.6 kg |
| Pregelatinized Starch NF | 27.7 kg |
| Purified Water USP | 86.0 gallons |
| Dry Ingredients (In product bowl) | |
| Acetaminophen, USP | 400.0 kg |
| Pregelatinized Starch, NF | 13.9 kg |
| Post Granulation | |
| Stearic Acid, NF | 2.25 kg |

Process conditions were as follows:

| Machine Parameters | |
|---|---|
| Inlet Flap | 100% |

-continued

| Machine Parameters | |
|---|---|
| Outlet Flap | 60–79% |
| Nozzle Height | Position 16 |
| Nozzle Type | 3 head with 2.2 mm inserts |
| Atomizing Air Pressure | 5 bar |
| Spray Interval | 90 seconds |
| Shake Interval | 5 seconds |
| Spray Rate | 2000–3000 ml/minute |
| Inlet Temperature | 44–64° C. |
| Outlet Temperature | 21–30° C. |
| Product Temperature | 24–30° C. |

The granulated product had the following characteristics:

| Moisture = 1.7% | |
|---|---|
| Bulk Density = 0.59 g/cc | |
| Particle Size: | |
| Screen (Mesh size) | Percent Retained |
| 20 | 49.6% |
| 40 | 94.8% |
| 60 | 98.6% |
| 80 | 98.8% |

Assay - 90.6%

Generally, when an additional binding agent is used, a smaller amount of the pregelatinized starch is added dry, for example, about 2.0–5.0 weight percent. The remaining pregelatinized starch and the additional binder are dispersed together and then sprayed onto the fluid bed as outlined above.

To achieve desired tablet disintegration and dissolution properties, a pharmaceutically acceptable disintegrant may be incorporated in the above formulations.

The use of auxillary binders is not limited to the ones mentioned here but, most pharmaceutically acceptable binding agents may work satisfactorily in the above compositions.

TABLE I

| Typical Tablet Properties for Example I | | |
|---|---|---|
| Tablet weight (theoretical) | 555.5 mg | 361.1 mg |
| Tablet Hardness (Kp)[1] | 9.5 | 8.0 |
| Max | 16.0 | 14.0 |
| Tablet Diameter | 7/16 inch | 13/32 inch |
| Tablet Disintegration Time (Min.) | Less Than 5 minutes (for 9.5 Kp tablets) | Less Than 5 minutes (for 8.0 Kp tablets) |
| Tablet Dissolution ($T_{80}$)[2] | <10 minutes (for 9.5 Kp tablets) | <10 minutes (for 8.0 Kp tablets) |
| Tablet Friability[3] | 0.5% | 0.5% |

[1] Schleuniger Hardness Tester
[2] USP method for Acetaminophen Tablets
[3] Roche Friabulator.

TABLE II

Tablet Characteristics for Example 4

Tablet weight 555 mg/tablet
APAP 500 mg/tablet
Tooling = 15/32 inch diameter flat face bevel edge tooling
Hardness Maximum = 14.3 kp
Characteristics for tablets of 10.5 kp
Thickness = 0.176 inch
Friability = 0.2%

TABLE II-continued

Tablet Characteristics for Example 4

Disintegration Time = <5 minutes

It is understood that the foregoing detailed description is given merely by way of illustration and that many modifications may be made therein without departing from the spirit or scope of the present invention.

We claim:

1. A particulate N-acetyl-p-aminophenol composition useful in the preparation of tablets having high hardness, short disintegration time and short dissolution time, the composition being devoid of a lubricant and comprising as components thereof:
    (a) from about 84 to 94 percent, based on the dry weight of the composition, of N-acetyl-p-aminophenol,
    (b) from about 5 to about 15 percent, based on the dry weight of the composition, of a pharmaceutically acceptable pregelatinized starch, and
    (c) water,
said composition being prepared in a fluid bed granulator-dryer by the process which comprises spraying an aqueous slurry of a portion of the pregelatinized starch onto a fluidized composition comprising N-acetyl-p-aminophenol and the remainder of the pregelatinized starch; and drying the resulting granules to a moisture level of from about 1.0 to about 2.5 percent.

2. A particulate N-acetyl-p-aminophenol composition as claimed in claim 1, wherein the composition further comprises a pharmaceutically-acceptable compressibility-promoting binder as a binding agent.

3. A particulate N-acetyl-p-aminophenol composition as claimed in claim 2, wherein the compressibility-promoting binder is polyvinylpyrrolidone.

4. A particulate N-acetyl-p-aminophenol composition as claimed in claim 2, wherein the compressibility-promoting binder is present in an amount from about 0.5 parts to about 2.5 parts per 100 parts of the composition.

5. A method for producing a particulate N-acetyl-p-aminophenol composition useful in the preparation of tablets having high hardness, short disintegration time and short dissolution time, the method comprising:
    (a) charging the N-acetyl-p-aminophenol and a quantity of pregelatinized starch to a fluid bed granulator-dryer,
    (b) fluidizing the materials in the granulator-dryer until thoroughly blended,
    (c) dispersing a quantity of pregelatinized starch in water to form a slurry having from about 5 to about 10 percent by weight solids,
    (d) spraying the starch dispersion so formed onto the fluidized bed of N-acetyl-p-aminophenol and pregelatinized starch at a rate sufficient to maintain the powder bed moisture between about 5 and about 20 percent by weight,
    (e) continuing drying after all the dispersion is sprayed onto the bed to reach a bed moisture from about 1.0 to about 2.5 percent by weight, and
    (f) sizing the material to a desired particle size distribution.

6. The method of claim 5, wherein there is also charged to the fluid bed granulator-dryer a pharmaceutically acceptable compressibility-promoting binder.

7. The method of claim 6, wherein the compressibility-promoting binder is polyvinylpyrrolidone.

* * * * *